(12) United States Patent
Kratzberg et al.

(10) Patent No.: US 8,876,849 B2
(45) Date of Patent: Nov. 4, 2014

(54) FALSE LUMEN OCCLUDER

(75) Inventors: Jarin Kratzberg, Lafayette, IN (US);
Sharath Gopal, Bangalore (IN); James D. Purdy, Lafayette, IN (US); Blayne A. Roeder, Lafayette, IN (US); Steven J. Charlebois, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 188 days.

(21) Appl. No.: 13/170,843

(22) Filed: Jun. 28, 2011

(65) Prior Publication Data

US 2012/0022573 A1    Jan. 26, 2012

Related U.S. Application Data

(60) Provisional application No. 61/365,955, filed on Jul. 20, 2010.

(51) Int. Cl.
*A61M 29/00* (2006.01)
*A61B 17/12* (2006.01)

(52) U.S. Cl.
CPC ..... *A61B 17/12022* (2013.01); *A61B 17/12172* (2013.01); *A61B 17/12113* (2013.01)
USPC ............................. 606/191; 606/200; 128/887

(58) Field of Classification Search
USPC .............. 606/108, 191, 194, 200; 128/887; 623/1.11–1.54
See application file for complete search history.

(56) References Cited

U.S. PATENT DOCUMENTS

| | | | |
|---|---|---|---|
| 4,619,246 A | 10/1986 | Molgaard-Nielsen et al. | ... 128/1 R |
| 5,234,458 A | 8/1993 | Metais | 606/200 |
| 5,382,259 A | 1/1995 | Phelps et al. | 606/151 |
| 5,916,235 A | 6/1999 | Guglielmi | 606/200 |
| 5,976,174 A | 11/1999 | Ruiz | 606/213 |
| 6,193,708 B1 | 2/2001 | Ken et al. | 606/1 |
| 6,346,117 B1 | 2/2002 | Greenhalgh | 606/200 |
| 6,368,338 B1 | 4/2002 | Konya et al. | 606/200 |
| 6,428,558 B1 | 8/2002 | Jones et al. | 606/200 |
| 6,636,068 B2 | 10/2003 | Farnworth et al. | 324/765 |
| 6,740,331 B1 | 5/2004 | Bates et al. | 424/423 |
| 6,746,468 B1 | 6/2004 | Sepetka et al. | 606/200 |
| 7,648,495 B2 | 1/2010 | Bates | 604/890.1 |
| 2005/0165442 A1* | 7/2005 | Thinnes et al. | 606/200 |
| 2007/0233178 A1* | 10/2007 | Gilson et al. | 606/200 |
| 2009/0138035 A1 | 5/2009 | Isshiki et al. | 606/200 |

FOREIGN PATENT DOCUMENTS

| | | | |
|---|---|---|---|
| EP | 0 882 428 A2 | 5/1998 | ............. A61B 17/12 |
| WO | WO 99/12484 | 8/1998 | ............. A61B 17/12 |

* cited by examiner

*Primary Examiner* — Kathleen Holwerda
(74) *Attorney, Agent, or Firm* — Brinks Gilson & Lione

(57) ABSTRACT

An endoluminal device for repairing an aortic dissection and preventing future aortic dissections, the device including a plurality of struts with at least one of the plurality of struts having a mid-strut portion having two or more secondary struts, the device being configured to be secured within a false lumen of the aorta and contain filler material in order to encourage thrombosis within the false lumen.

20 Claims, 12 Drawing Sheets

FALSE LUMEN OCCLUDER

BACKGROUND

Aortic dissection is a condition that affects the aorta, which is the largest artery in the body. This condition is caused by the separating/dissection of the individual layers of the aorta, where the inner layer of the aortic wall tears, or peels, away from the adjacent layer of the aorta. This separation of the layers creates an area, or a pathway, between the torn-away layer and the remainder of the aortic wall. The area created by the two layers is called a false lumen. As blood flows through the aorta, it travels through its normal pathway, referred to as the true lumen, but a portion of the blood also is directed into the false lumen.

The false lumen is a secondary flow path that does not provide any blood delivery to the remainder of the body. As blood continues to be diverted into the false lumen, the rate of blood flow and volume of diverted blood into the false lumen can result in the exertion of large forces against the aortic wall. These forces result in the further propagation of the tear, thereby creating a larger false lumen and greater associated forces. The propagation of the tear can eventually lead the aorta wall to rupture, which can result in death.

The type of treatment for this condition depends on the severity and location of the aortic tear. Medical therapy, such as blood pressure and cholesterol-lowering drugs, are typically provided as one method of treatment for this condition. Medical therapy is designed to limit further propagation of the tear and to reduce the chances of aortic rupture. This type of treatment is adequate when the condition is in its early stages and no significant tear exists. However, it is not designed to prevent the further propagation of a dissected portion of the aortic wall.

In situations where the condition has progressed to a point where the risk of aortic rupture or further propagation is higher, more aggressive types of treatment may be required. Such additional types of treatment include endovascular intervention and open surgical repair. Endovascular intervention is a minimally invasive procedure where a stent graft is placed within the damaged area. When expanded, the stent graft exerts a radial force along the damaged area, thereby forcing the dissected layer of the aorta against the adjacent layer of the aortic wall. In theory, retaining the dissected layer of the aorta against the adjacent layer of the aortic wall prevents blood from flowing into the dissected layer, thereby minimizing the blood flow into the false lumen. This type of treatment, however, only covers the dissected layer and sometimes does not fully occlude the false lumen formed between the dissected layer and the adjacent layer of the aortic wall. As a result, and typically in chronic aortic dissection cases, there is a likelihood that blood will continue to flow between the dissected layer and the adjacent aortic layer, thereby causing the dissected portion of the aortic wall to further separate from the adjacent layer of the aortic wall which allows additional blood to reenter the false lumen. Another disadvantage of this type of treatment is that it does not prevent the chances of future tears in the damaged area. As a result, endovascular repair is an inadequate method of treatment for patients suffering from chronic aortic dissection.

Open surgical repair is another type of treatment used to cure aortic dissection. This highly invasive procedure requires the replacement of the diseased portion of the aorta with a Dacron/ePTFE graft. The graft is sewn in the place of the removed portion of the aorta and on average requires a two-month recovery period. As true with other highly invasive medical procedures, open surgical repair is a lengthy procedure and subjects patients to a higher risk for stroke, ischemia, and other medical complications. As a result, this type of procedure is not recommended to treat aortic dissection cases unless no other treatment is available and carries a high likelihood of post-surgical complications.

Therefore, there is a need for another type of medical treatment to prevent against chronic aortic dissection while minimizing the complications related to open surgical treatment.

BRIEF SUMMARY

In one embodiment of the present invention, the intraluminal device comprises a first end, a second end, and a central longitudinal axis between the first and second ends and expanded and compressed configurations, where a plurality of struts extend from the first to second end of the intraluminal device with at least one of the struts having a proximal strut portion, a distal strut portion, and a mid-strut portion between the proximal strut portion and the distal strut portion, where the mid-strut portion has at least two struts, and when the intraluminal device is in the expanded configuration, the plurality of struts are biased away from the longitudinal axis.

In another embodiment of the present invention, the intraluminal device comprises a first end, a second end, and a central longitudinal axis between the first and second ends and a expanded and compressed configurations, where a plurality of struts made from the same piece of material extend from the first to second end of the intraluminal device with at least one of the struts having a proximal strut portion, a distal strut portion, and a mid-strut portion between the proximal strut portion and the distal strut portion, where the mid-strut portion has at least two struts, and when the intraluminal device is in the expanded configuration, the plurality of struts are biased away from the longitudinal axis and the at least two struts of the mid-strut portion have an arcuate shape.

In yet another embodiment of the present invention, the intraluminal device comprises a first end, a second end, and a central longitudinal axis between the first and second ends and expanded and compressed configurations, where a plurality of struts made from the same piece of material extend from the first to second end of the intraluminal device with at least one of the struts having a proximal strut portion, a distal strut portion, and a mid-strut portion between the proximal strut portion and the distal strut portion, where the mid-strut portion has at least two struts made out of the same material as the plurality of struts, and when the intraluminal device is in the expanded configuration, the plurality of struts are biased away from the longitudinal axis and the at least two struts of the mid-strut portion have an arcuate shape.

DETAILED DESCRIPTION OF THE DRAWINGS AND THE PRESENTLY PREFERRED EMBODIMENTS

Figure 1:
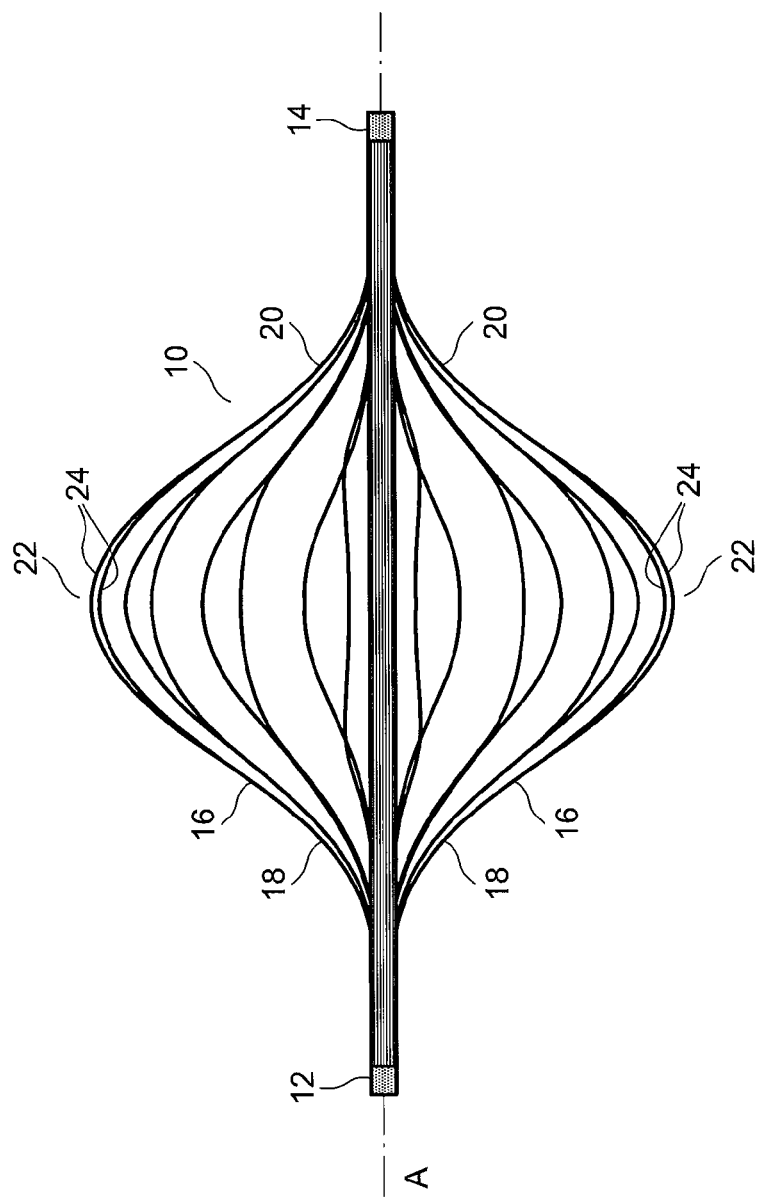
FIG. 1 shows a side view of one embodiment of an intraluminal device having a plurality of struts in an expanded configuration.

To help understand this invention, the following definitions are provided with reference to terms used in this application.

Throughout this specification and in the appended claims, when discussing the application of this invention with respect to the aorta or other blood vessels, the term "distal" with respect to such a device, or false lumen occluder, is intended to refer to a location that is, or a portion of the device that when implanted, is further downstream with respect to blood flow; the term "distally" means in the direction of blood flow or further downstream. The term "proximal" is intended to refer to a location that is, or a portion of the device that when implanted is, further upstream with respect to blood flow; the term "proximally" means in the direction opposite to the direction of blood flow or further upstream.

The term "intraluminal" describes objects that are found or can be placed inside a lumen in the human or animal body. A lumen can be an existing lumen or a lumen created by surgical intervention. This includes lumens such as blood vessels, such as an aorta, parts of the gastrointestinal tract, ducts such as bile ducts, parts of the respiratory system, etcetera. "Intraluminal device" is thus a device that can be placed inside one of these lumens. An expandable device having a plurality of struts is a type of intraluminal device.

The embodiments below are described with reference to the drawings in which like elements are referred to by like numerals. The relationship and functioning of the various elements are better understood by the following detailed description. However, the embodiments as described below are by way of example only, and the invention is not limited to the embodiments illustrated in the drawings.

This invention relates to an intraluminal device having a plurality of struts extending from a first end of the device to the second end of the device. Along at least one of the struts is a mid-strut portion having two secondary struts. The method of delivery and placement of the intraluminal device within a lumen is also part of the invention described herein.

In the preferred embodiment, shown in FIG. 1, an intraluminal device 10 in an expanded configuration is shown. The intraluminal device 10 includes a first end 12 and a second end 14, where the first end 12 and second end 14 are along a central longitudinal axis A. A plurality of struts 16 extend from the first end 12 to the second end 14 and are made out of a single piece of material. Each of the plurality of struts 16 include a proximal portion 18 that is adjacent to the first end 12 and a distal portion 20 that is adjacent to the second end 14 of the intraluminal device 10. In this embodiment, there are 16 struts 16, however the number of struts 16 in a particular embodiment may vary and can range anywhere between 10 and 25.

As further shown in FIG. 1, each of the plurality of struts 16 further includes a mid-strut portion 22. The mid-strut portion 22 is located between the proximal strut portion 18 and the distal strut portion 20 for each strut 16 of the plurality of struts. In this embodiment, the mid-strut portion 22 of the strut 16 comprises two secondary struts 24 that diverge from the proximal portion 18 of the strut 16 and converge into the distal portion 20 of the same strut 16. The number of secondary struts 24 per each mid-strut portion 22 can vary anywhere between two, which is shown in the embodiment disclosed in FIG. 1, up to, and including, six. Moreover, a single strut 16 may also have more than one mid-strut portion 22, with each midstrut having two or more secondary struts 24 extending therefrom.

The secondary struts 24 permit expansion of the intraluminal device 10 to significantly larger diameters than would otherwise be possible with just a single strut, and also reduce the extent of foreshortening the intraluminal device 10 undergoes upon expansion. The secondary struts 24 also contribute to enhanced stiffness of the intraluminal device 10 during loading, deployment and in vivo. Further, the secondary struts 24 increase the amount of metal in the intraluminal device 10 without contributing to the overall stiffness.

It can be appreciated that the number of secondary struts 24 in a particular embodiment may also vary. For example, it is contemplated that in one embodiment of the intraluminal device 10, one strut 16 may have zero secondary struts 24, another strut 16 may have two secondary struts 24, and yet another strut 16 may have four secondary struts 24, and so forth.

The relative locations and lengths of the mid-strut portion 22 with respect to the proximal stent portion 18 and distal stent portion 20 may vary and is application dependent. For example, depending on the desired location of secondary struts 24 relative to the first end 12 and the second end 14 of the intraluminal device 10, the mid-strut portion 22 may be closer to one of the ends 12, 14. In addition, the length of each of the secondary struts 24 may also vary depending on the intended application. For example, in the embodiment shown in FIG. 1, the mid-strut portion 22 is approximately one half the overall length of the strut 16. This ratio may change depending on a particular application.

Figure 2:
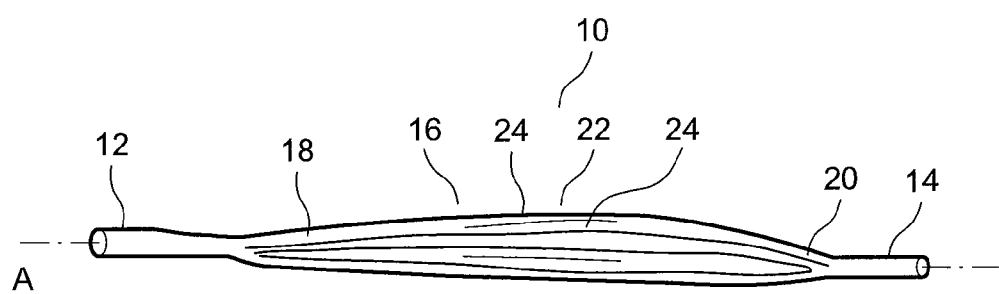
FIG. 2 shows a side view the intraluminal device shown in FIG. 1 in a compressed configuration.

The struts 16 of the intraluminal device 10 are configured to expand and compress such that the struts 16 are substantially parallel to the longitudinal axis A when in the compressed configuration. FIG. 2 depicts the intraluminal device 10 shown in FIG. 1 in a compressed configuration, where the struts 16 are substantially parallel to one another. When in the expanded configuration, the intraluminal device 10 may have a length anywhere between 10-80 mm and an outer diameter of anywhere between 5-50 mm. When in the compressed configuration, the length can vary from anywhere between 10-150 mm and have a compressed outer diameter of anywhere between about 5-18 Fr. The intraluminal device 10 is intended to have minimal radial force (just enough to enable deployment within the false lumen). The pattern shown in the preferred embodiment disclosed in FIG. 1 lends itself to this design goal. Specifically, the pattern shown in FIG. 1 is laser cut from a drawn, seamless tube, expanded to its final diameter and heat-set to retain the expanded shape. The pattern consists of a series of struts 16 that run parallel to the long axis of the intraluminal device 10, without any circumferential interconnections. The struts 16 are bifurcated at approximately ⅓rd the distance from either end 12, 14 of the intraluminal device 10 to form a pair of secondary struts 24, intended to enhance stability. The lack of circumferential interconnections is intended to reduce radial force and crush resistance.

In addition, the forces required to compress the pattern into its compressed configuration (during loading) are minimized as well. In its operational state, the intraluminal device 10 is intended to have radial and flat plate crush resistance less than a typical stent graft (e.g., less than 15 N) used for treatment of aortic aneurysms or dissections. This is essential to promote thrombosis of the false lumen and stabilization and opening of the true lumen as the blood flow increases through the lumen.

The size and shape of the struts 16 and secondary struts 24 may vary depending on a particular application. In the preferred embodiment shown in FIGS. 1 and 2, each strut 16 has a length of 20 mm and a width of 220 µm and each of the two secondary struts 24 has a length of approximately 25 mm and a width of approximately 92 µm. When in the expanded configuration, each of the two secondary struts 24 and form a 40 mm opening, or luminal diameter, 66 therebetween.

It can be appreciated that the dimensions of the secondary struts 24 of a particular strut 16 may depend on the number of secondary struts 24 for that particular embodiment. For example, if a particular strut 16 has two secondary struts 24, the width of each secondary strut will approximately be one half of the width of the strut 16. And if a particular strut 16 has three secondary struts 24, the width of each secondary strut 24 will approximately be one third of the width of the strut 16. However, this relationship between the number of secondary struts 24 and the width of the primary strut 16 is not required and there also may be instances where the width of each of the secondary struts 24 for a particular strut 16 may be not be equal to one another.

Figure 3:
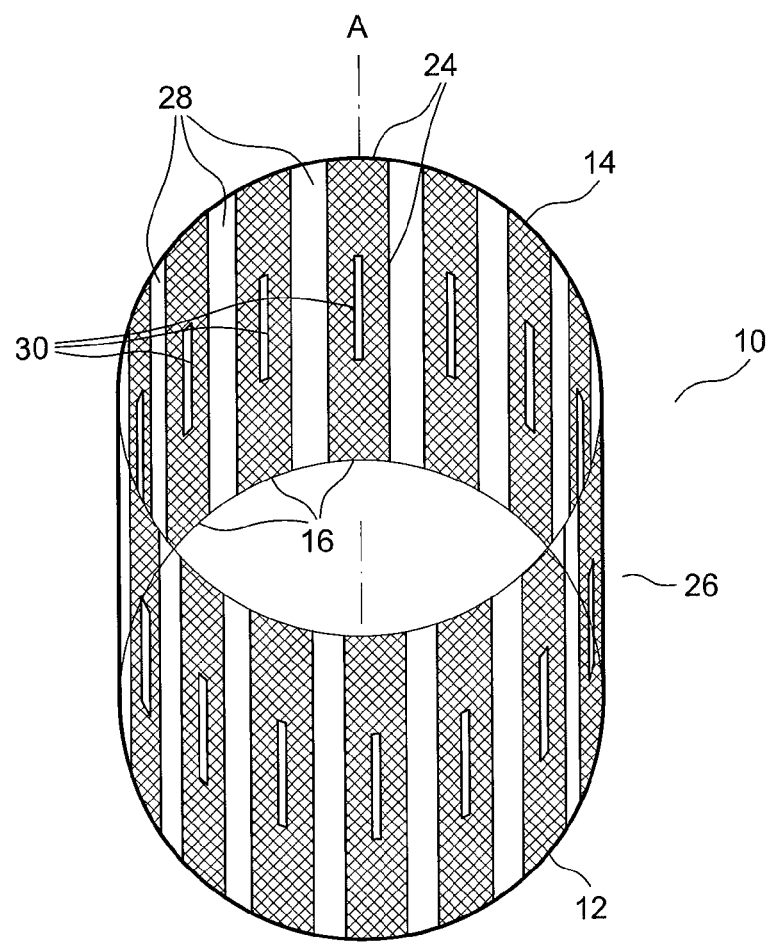
FIG. 3 shows a front view of the intraluminal device shown in FIG. 1 when in the compressed configuration.

In the embodiment shown in FIGS. 1 and 2, the intraluminal device 10 is made out of a single piece of material. The types of material from which the intraluminal device 10 may be manufactured include a shape memory alloy comprised of Nickel and Titanium, which is commonly referred to as Nitinol, and Teritary alloys. As shown in FIG. 3, the intraluminal device 10 in this embodiment is manufactured out of a single cylindrical tube 26. The cylindrical tube 26 has a plurality of primary cuts 28 formed along the longitudinal axis A. The primary cuts 28 form the struts 16 of the intraluminal device 10. Between each primary cut 28 is a secondary cut 30, which also extends along the longitudinal axis A. As shown in FIG. 3, the secondary cuts 30 are not as long and wide as the primary cuts 28 and form the secondary struts 24 of the intraluminal device 10. In this embodiment, the struts 16 and the secondary struts 24 have a rectangular-shaped cross-section.

The dimensions of the cuts 28, 30 may vary between embodiments and within a single embodiment. For example, the respective lengths of each of the primary cuts 28 and secondary cuts 30 may vary in a single embodiment and the width of the cuts 28, 30 may vary along a single cut, such that the width of the cut 28, 30 may increase from the first end 12 as it approaches the mid-strut portion 22 and then decrease as it approaches the second end 14, or vice versa, thereby affecting the shape and width of the struts 16, 24. As shown in FIG. 3, the path, or pattern, along which the cuts 28, 30 are made is substantially parallel to the longitudinal axis A. However, it is contemplated that the cuts 28, 30 may have a helical or a spiral-type path, or pattern, about the cylindrical tube 26.

Figure 4:
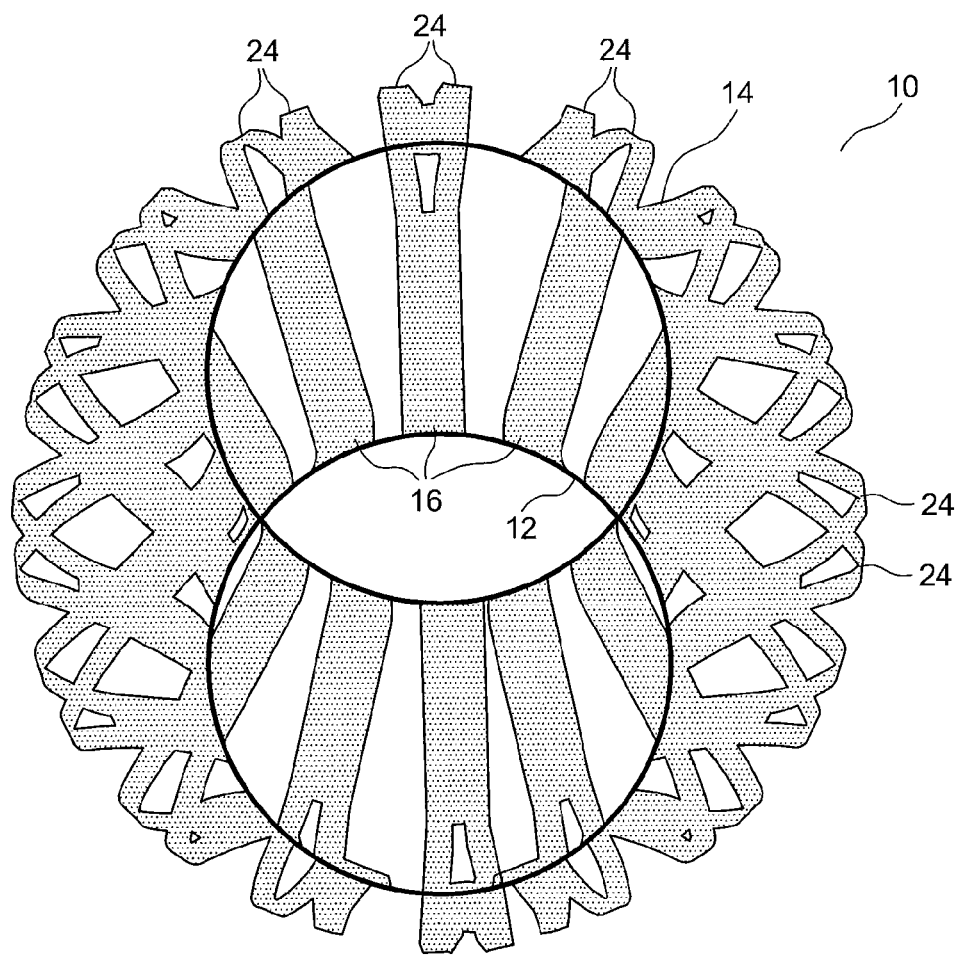
FIG. 4 shows a front view of the intraluminal device shown in FIG. 1 when in the expanded configuration.

FIG. 4 is the intraluminal device 10 shown in FIG. 3 in the expanded configuration. As shown in this figure, when in the expanded configuration, the struts 16 have an arcuate shape that bows away from the longitudinal axis A, and the secondary struts 24 of each strut 16 bias or bend away from one another. The secondary struts 24 may bias away from each other in directions relative to the longitudinal axis, for example radially inward and outward. For example, one secondary strut 24 may bias toward the axis and the other away from the axis. Alternatively, and preferably, the secondary struts 24 may bias away from the longitudinal axis A and from one another in a radial direction. When in the expanded configuration, the intraluminal device 10 is ellipsoidal in shape. It is contemplated that the intraluminal device 10 may have other shapes, such as a spherical shape, depending on the geometry and pattern of the struts 16, 24. When in the expanded configuration, the overall length of the intraluminal device 10 is less than when in the compressed configuration, and the maximum outside diameter of the intraluminal device 10 is greater than when in the compressed configuration.

Figure 5:
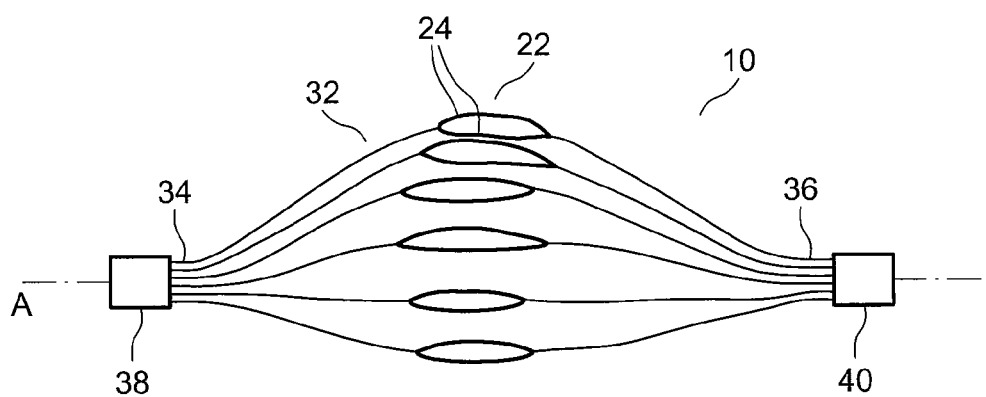
FIG. 5 shows another embodiment of the intraluminal device having a plurality of independent struts in an expanded configuration.

In an alternative embodiment, shown in FIG. 5, the intraluminal device 10 is made of a plurality of independent struts 32, each having a first end 34 and a second end 36. In this embodiment, each of the first ends 34 of the independent struts 32 are held together via a first hub 38 and each of the second ends 36 of the independent struts 32 are held together via a second hub 40. The independent struts 32 in this embodiment may also have a mid-strut portion with secondary struts that is substantially the same as the mid-strut portion 22 and secondary struts 24 described above with respect to the first embodiments.

Figure 6:
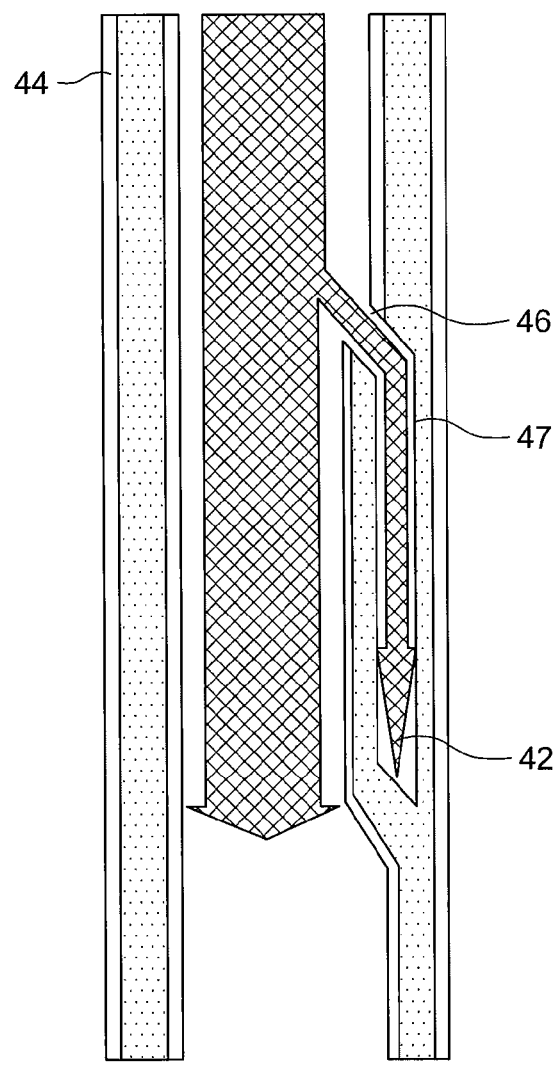
FIG. 6 shows a cross-sectional view of a false lumen within the aorta.

The intraluminal device 10 is intended to be placed into false lumen 42 of an aorta 44, a pictorial representation of which is shown in FIG. 6. The false lumen 42 is a pocket created by a tear in the lining 46 of the aortic wall. A portion of the aortic lining 46 separates from an adjacent portion of the aortic lining 47 thereby forming a pocket. Blood flow is partially diverted into this pocket thereby creating a false lumen 42. The pressure of the blood flow and collection of blood in this lumen 42 can cause the torn portion of the aortic lining 46 to propagate and eventually lead to the rupture of the aortic wall.

Figure 7:
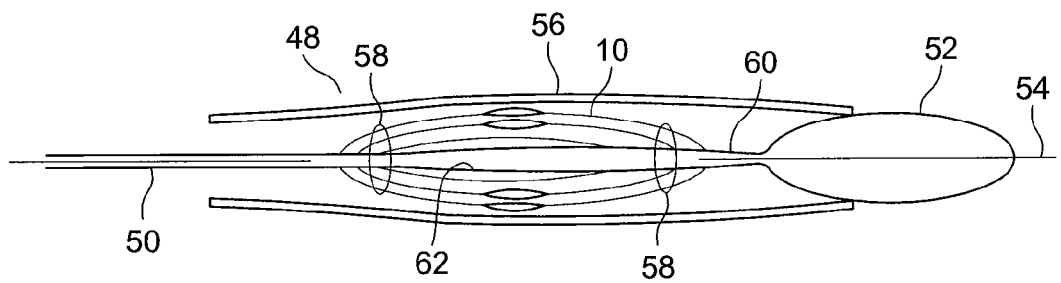
FIG. 7 shows one embodiment of a deployment device for the intraluminal device.

As shown in FIG. 7, the intraluminal device 10 is loaded onto a deployment device 48 for insertion into a vessel. The deployment device 48 includes a guide wire catheter 50 having a first end 60 with a nose cone dilator 52 attached thereto. The intraluminal device 10 is located along a body 62 of the guide wire catheter 50 and may be radially compressed and secured thereto by two trigger wires 58, which form loops around the intraluminal device 10. A sheath 56 is disposed over the guide wire catheter 50 and intraluminal device 10. The sheath 56 assists the trigger wires 58 in retaining the intraluminal device 10 in the compressed configuration prior to deployment. Note that the sheath 56 alone may be sufficient to retain the intraluminal device 10 to the body 62 of the catheter 50. The superelastic property of Nitinol allows the struts 16, 24 of the intraluminal device 10 to undergo considerable deformation, such as radial compression, yet return to their original shape when the compression force is removed. In the preferred embodiment, a formulation of Nitinol comprising about 49.5% to 51.5% Nickel (atomic %) and about 50.5% to 48.5% Titanium is used (atomic %). Preferably, an equiatmoic formulation of Nitinol is used. Additional formulations, consisting of ternary alloys (e.g. Nitinol doped with 0.25 at % Chromium) may be used. As a result of the superelastic property, the intraluminal device 10 may be placed in a compressed or collapsed configuration as shown in FIG. 9, yet expand back to its original configuration when deployed from the deployment device 48 within the vessel.

Figure 8:
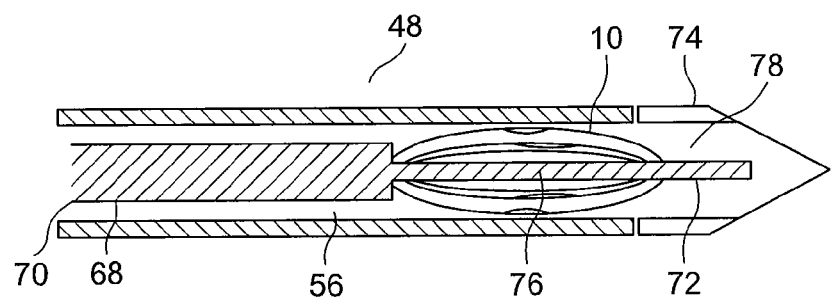
FIG. 8 shows another embodiment of the deployment device of the intraluminal device.

In an another embodiment, the deployment device 48, as shown in FIG. 8, includes a guide wire catheter 68 having a first end 70 and a second end 72 and a reduced diameter portion 76 adjacent to the second end 72. A cap 74 is disposed on the second end 72 and forms part of the guide wire catheter 68. The cap 74 forms a cavity 78 between it and the second end 72 in which a portion of the intraluminal device 10 may reside in the compressed configuration. Prior to deployment, the intraluminal device 10 is positioned along the reduced diameter portion 76 and is retained by a sheath 56 and the cap 74 such that the intraluminal device 10 is retained in the compressed configuration.

Figure 9:
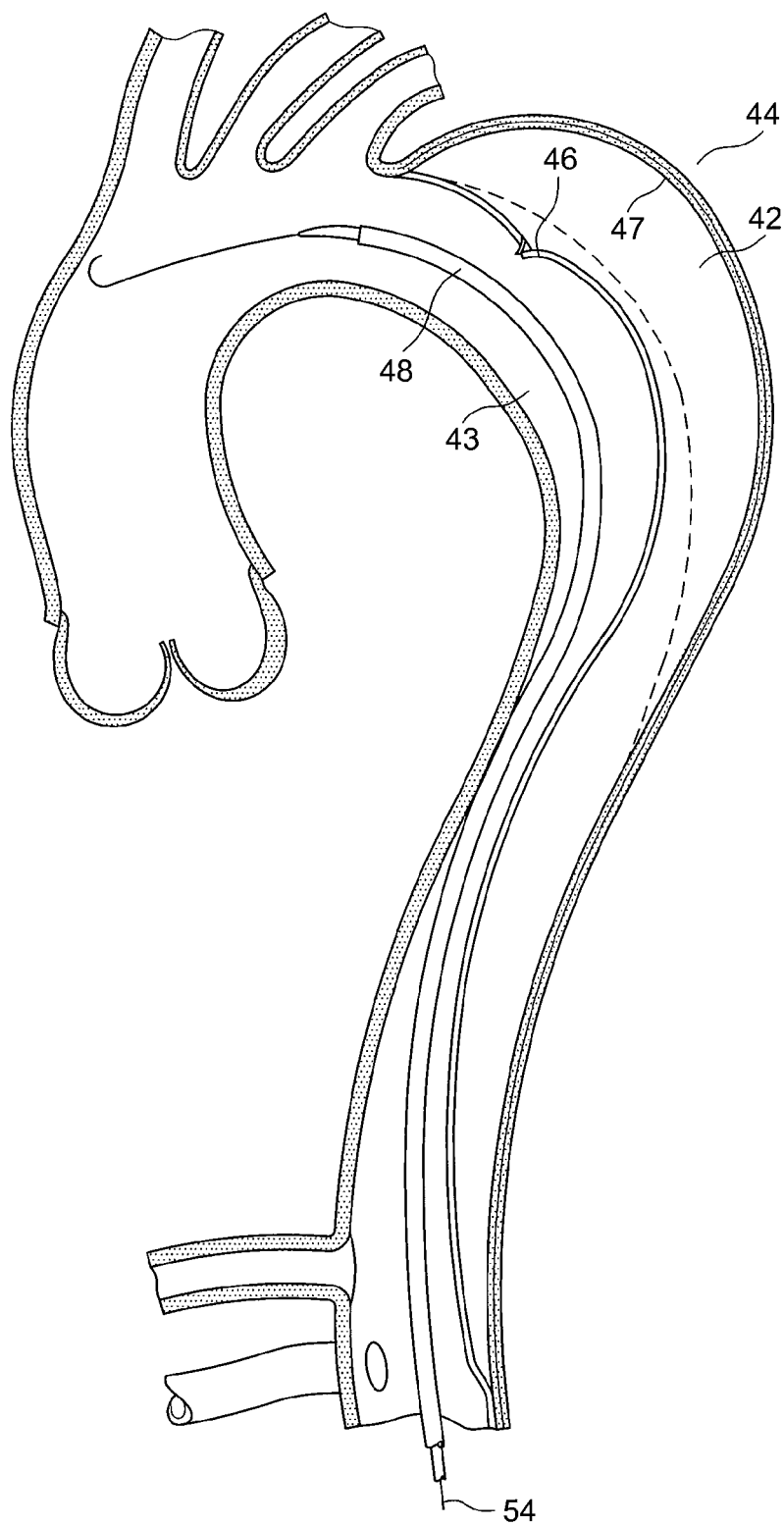
FIG. 9 shows the deployment device entering a vessel and a false lumen within the aorta.
Figure 10:
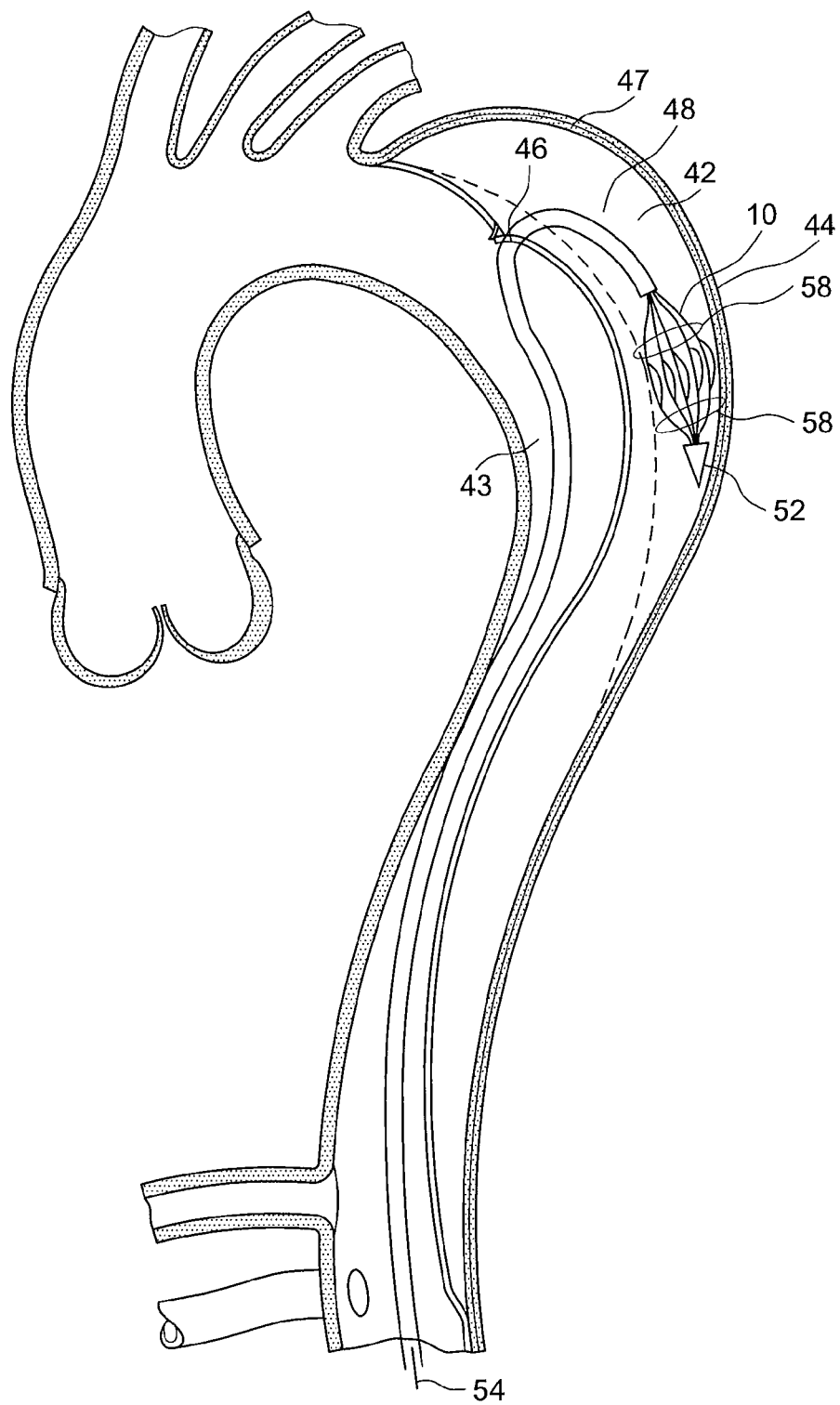
FIG. 10 shows the deployment of the intraluminal device within the false lumen shown in FIG. 9.
Figure 11:
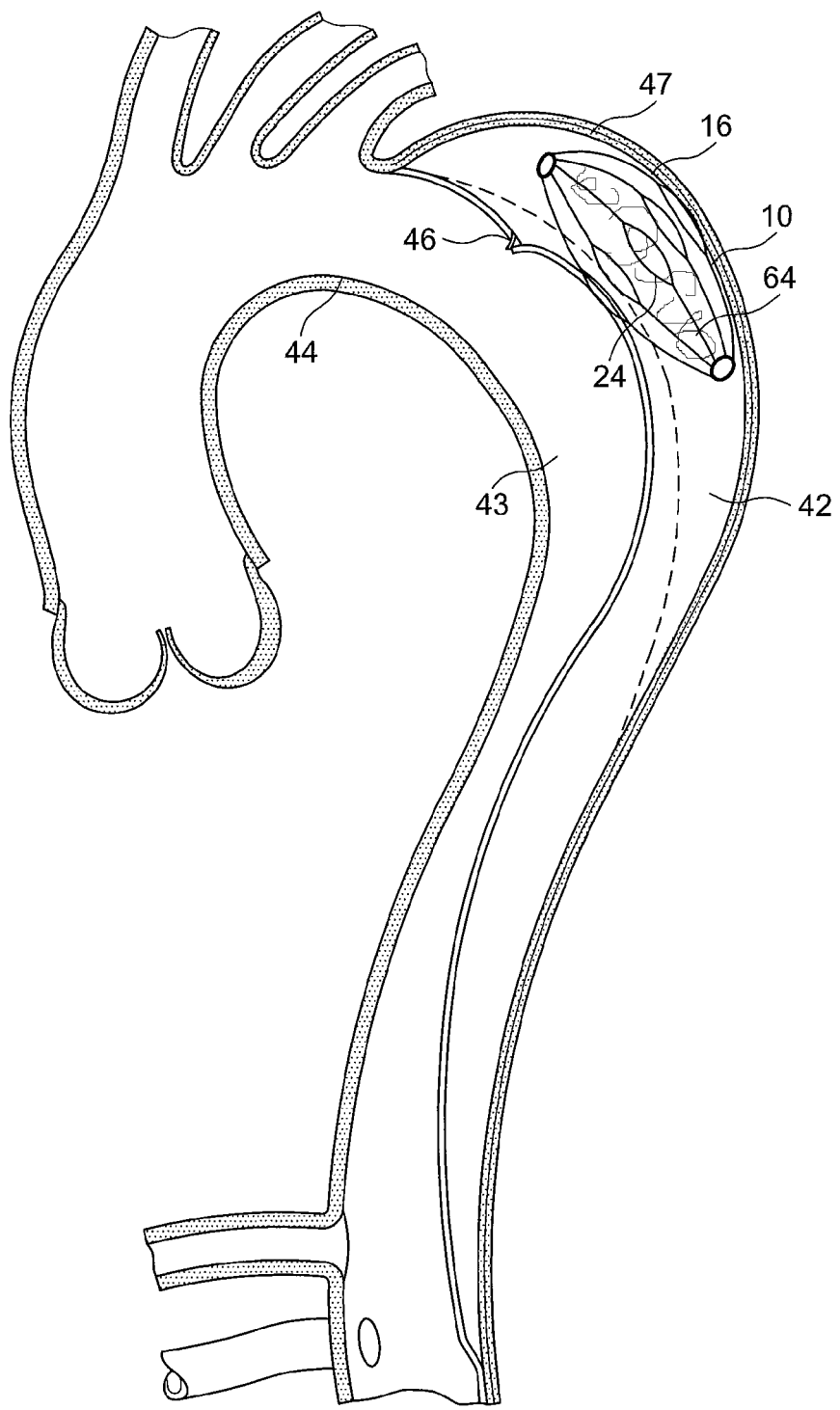
FIG. 11 shows the intraluminal device secured within the false lumen shown in FIG. 9.

FIGS. 9-11 depict the deployment of the intraluminal device 10 within a blood vessel, which in this instance is the aorta 44. As shown in FIG. 9, a guide wire 54 is inserted through a femoral artery and is positioned within or adjacent to the false lumen 42. Alternatively, the guide wire 54 may be introduced via the subclavin artery into the aortic arch and positioned within or adjacent to the false lumen 42. In either scenario, the deployment device 48 is inserted along the guide wire 54 and positioned at a point of deployment within the false lumen 42. Once the deployment device 48 reaches the desired point of deployment, the sheath 56 is retracted, as shown in FIG. 10. Finally, the trigger wires 58 securing the intraluminal device 10 to the body 62 of the guide wire catheter 48 are disengaged from the intraluminal device 10.

As the sheath 56 retracts, the intraluminal device 10 expands from its compressed configuration to its expanded configuration, as shown in FIG. 11. In an alternative method of deployment, the sheath 56 may be retracted before the trigger wires 58 disengaged from the intraluminal device 10. In this scenario, the disengagement of the trigger wires 58 from the intraluminal device 10 will cause the intraluminal device 10 to expand into its expanded configuration as shown in FIG. 11. As discussed above, the outside diameter of the intraluminal device 10 when in the expanded configuration can range between about 5-50 mm, and the exact diameter is determined by the size of the false lumen 42, which can vary anywhere between 5-20 mm. The radial force exerted by the struts 16, 24 of the intraluminal device 10 ranges from 0.1 to 10 N and helps secured the intraluminal device 10 within the false lumen 42.

Once the intraluminal device 10 is in the expanded configuration and secured within the false lumen 42, a filler material 64 may be inserted into the void formed by the expanded struts 16, 24. Examples of the filler material 64 include: embolization coils, small intestinal submucosa (SIS), hydrogels, PETE, such as Dacron®, and microspheres. MReye® is one type of embolization coil that may be inserted into the intraluminal device 10. MReye® is used for arterial and venous embolization in the peripheral vasculature and is manufactured by Cook Medical Inc., located in Bloomington, Ind. The filler material 64 may be inserted into the cavity by a second catheter or through the same deployment device 48 that deployed the intraluminal device 10 within the false lumen 42. In the alternative, the filler material 64 may be disposed within the intraluminal device 10 prior to being loaded onto the deployment device 48.

Figure 12:
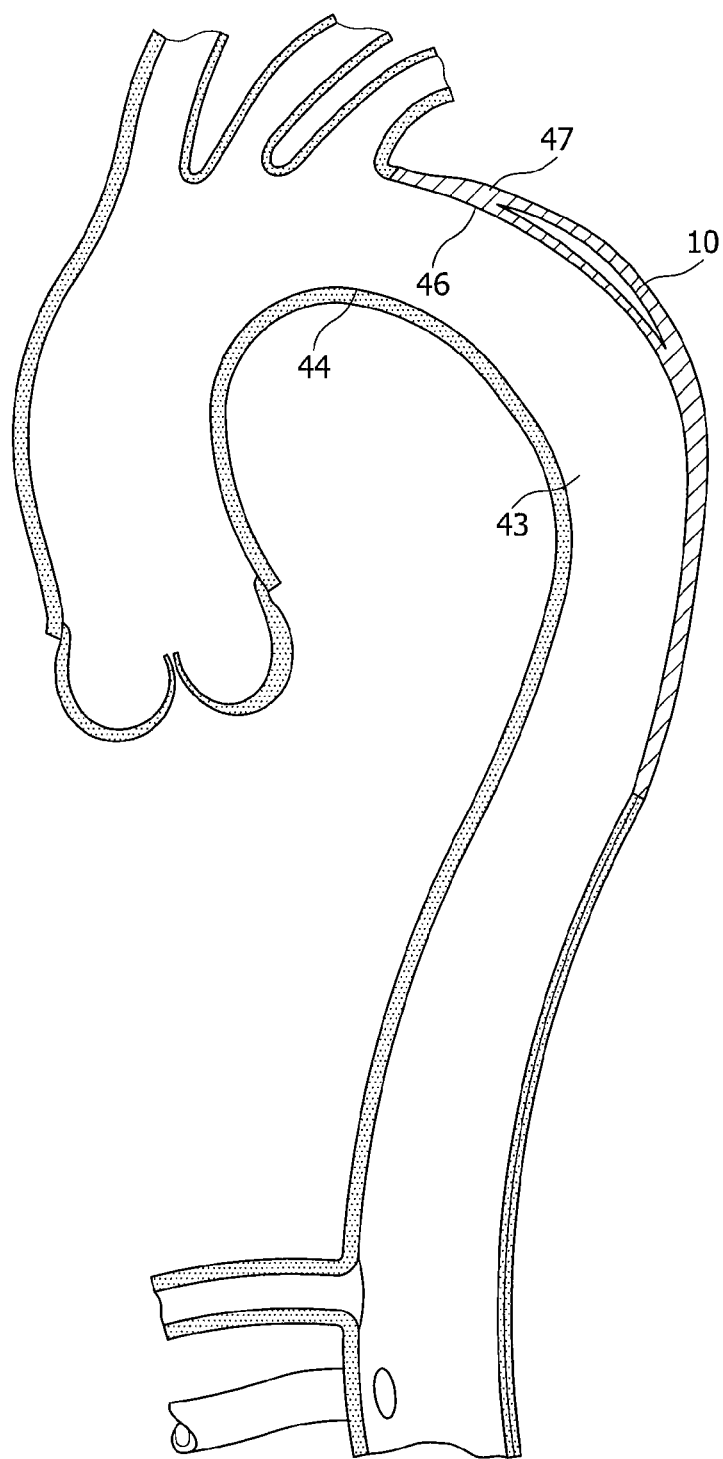
FIG. 12 shows the intraluminal device in a compressed configuration within the false lumen shown in FIG. 9.

The filler material 64 within the intraluminal device 10 encourages the thrombotic process to occur within the false lumen 42. In some instances, once the intraluminal device 10 is placed within the false lumen 42, an endovascular stent or a stent graft may be placed in the true lumen 43 in order to retain the patency of the true lumen 43 and encourage the thrombotic process. Thrombosis will occur as a result of the filler material 64 causing turbulence and/or stagnation in the blood flow in the false lumen 42. Over time, the thrombosed area will grow, with the goal being to completely occlude the false lumen 42 from any pressurized blood blow. The blood flow will then be restored to the normal vessel pathway. As the vessel begins to heal, it will begin to remodel and strengthen and the true lumen 43 will stabilize and begin to expand. The expansion of the true lumen 43 will cause the false lumen 42 to collapse. The intraluminal device 10 has a low plate stiffness in the range of 0.1 to 10 N, which is far less than the radial force generated by the increased blood pressure exerted (or a stent graft that may be placed) within the true lumen 43. As a result, the intraluminal device 10 will begin to collapse as a result of the increased blood flow. The intraluminal device 10 will eventually achieve a low profile compressed configuration, as shown in FIG. 12.

Figure 13:
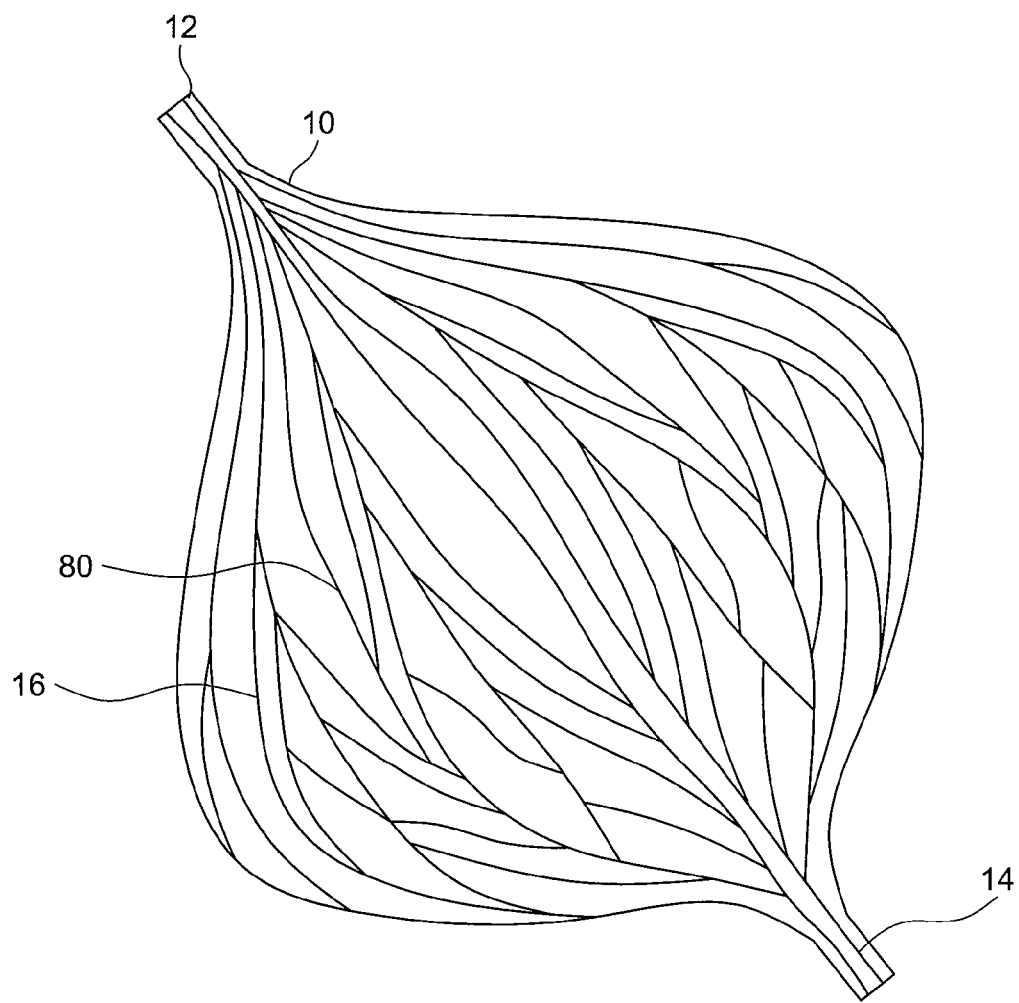
FIG. 13 shows another embodiment of the intraluminal device wrapped in a membrane.

In an alternate embodiment, the intraluminal device 10 is wrapped in a membrane 80, as shown in FIG. 13. In this embodiment, the membrane 80 is made out of a Dacron polymer fiber. The fibers are applied to the struts 16 of the intraluminal device 10 through a method referred to as electrospinning.

The membrane 80 prevents additional blood from entering the false lumen 42 and thereby decreasing the further propagation of the tear. The membrane 80 may be made out of any suitable fiber, or material, that exhibits substantially the same properties as Dacron, including a hemostatic type of collagen or SIS. The wrapping, or covering, process occurs via electrospinning when the intraluminal device 10 is in a compressed configuration. It is desired to perform the covering process when the intraluminal device 10 is in this configuration in order to prevent the covering to split apart when the intraluminal device 10 is compressed as it is loaded onto the deployment device. Otherwise, if the covering process was performed when the intraluminal device 10 was in a non-compressed configuration, the individual layers, or strands, of the membrane 80 would not be taught and would increase the likelihood of separating from one another during the loading process. In addition, a hemispherical ground plate is used during the electrospinning process to help attract fibers to the intraluminal device 10 being coated with the membrane 80. The hemispherical ground plate provides improved control of the location the fibers of the membrane 80 are coated on the intraluminal device 10.

While the present invention has been described in terms of preferred examples, and it will be understood that the invention is not limited thereto since modifications may be made to those skilled in the art, particularly in light of the foregoing teachings

The invention claimed is:
1. An intraluminal device comprising:
a first end;
a second end, the first and second ends of the device defining a longitudinal axis;
a plurality of struts extending from the first end to the second end; and
at least one of the plurality of struts comprising:
a proximal strut portion adjacent to the first end;
a distal strut portion adjacent to the second end; and
a mid-strut portion between the proximal strut portion and the distal strut portion, the mid-strut portion having at least two struts;
wherein when in an expanded configuration, the plurality of struts are biased away from one another, the at least two struts of the mid-strut portion are biased away from each other, where the plurality of struts converge towards the longitudinal axis at the second end, and where the device has a flat plate crush resistance that is less than 15 Newtons.

2. The intraluminal device of claim 1 wherein the at least two struts of the mid-strut portion have an arcuate shape when in the expanded configuration.

3. The intraluminal device of claim 2 wherein the plurality of struts are made from a single piece of material.

4. The intraluminal device of claim 1 further comprising a fill material disposed within the device, where the fill material is selected from the group consisting of small intestinal submucosa plugs, nitinol wire, Dacron fibers, and embolization coils.

5. The intraluminal device of claim 4 wherein the plurality of struts have a rectangular cross-section.

6. The intraluminal device of claim 5 wherein the at least two struts of the mid-strut portion have a rectangular cross-section.

7. The intraluminal device of claim 6 wherein when in the expanded configuration, the device has an outer diameter between about 5 mm and about 50 mm.

8. The intraluminal device of claim 7 wherein when in a compressed configuration, the device has an outer diameter between about 5 Fr to about 18 Fr.

9. The intraluminal device of claim 1 wherein the plurality of struts and the at least two struts of the mid strut portion are made out of the same piece of material.

10. The intraluminal device of claim 1 wherein the flat plate crush resistance is between approximately 0.1 to 10 Newtons.

11. An intraluminal device comprising:
a first end;
a second end, the first and second ends of the device defining a longitudinal axis; and
a plurality of struts extending from the first end to the second end, wherein the plurality of struts are made from the same piece of material;
wherein at least one of the plurality of struts comprises:
a proximal strut portion adjacent to the first end;
a distal strut portion adjacent to the second end; and
a mid-strut portion between the proximal strut portion and the distal strut portion, the mid-strut portion having at least two struts;
wherein when in an expanded configuration, the plurality of struts are biased away from one another, the at least two struts of the mid-strut portion have an arcuate shape, where the plurality of struts converge towards the longitudinal axis at the second end, and where the device has a flat plate crush resistance that is less than 15 Newtons.

12. The intraluminal device of claim 11 wherein each of the plurality of struts has a rectangular cross section.

13. The intraluminal device of claim 12 wherein each of the plurality of struts has a mid-strut portion having at least two struts.

14. The intraluminal device of claim 11 further comprising a fill material disposed within the device, where the fill material is selected from the group consisting of small intestinal submucosa plugs, nitinol wire, Dacron fibers, and embolization coils.

15. The intraluminal device of claim 14 wherein the width of each of the at least two struts of the mid-strut portion is approximately equal to one half of the width of the proximal strut portion of at least one of the plurality of struts.

16. The intraluminal device of claim 11 wherein the flat plate crush resistance is between approximately 0.1 to 10 Newtons.

17. An intraluminal device comprising:
a first end;
a second end, the first and second ends of the device defining a longitudinal axis; and
a plurality of struts extending from the first end to the second end of the device wherein the plurality of struts are made from the same piece of material;
at least one of the plurality of struts comprising:
a proximal strut portion adjacent to the first end;
a distal strut portion adjacent to the second end; and
a mid-strut portion between the proximal portion and the distal portion, the mid-strut portion having at least two diverging struts made out of the same piece of material as the plurality of struts;
wherein in an expanded configuration the plurality of struts are biased away from one another, the at least two struts of the mid-strut portion have an arcuate shape, where the plurality of struts converge towards the longitudinal axis at the second end, and where the device has a flat plate crush resistance that is less than 15 Newtons.

18. The intraluminal device of claim 17 wherein the flat plate crush resistance is between approximately 0.1 to 10 Newtons.

19. The intraluminal device of claim 18 wherein the length of each of the at least two struts of the mid-strut portion is approximately equal to one half of the overall length of the at least one of the plurality of struts.

20. The intraluminal device of claim 19 wherein the width of each of the at least two struts of the mid-strut portion is approximately equal to one half of the width of the proximal portion of the at least one of the plurality of struts.

* * * * *